(12) United States Patent
Richey, II

(10) Patent No.: US 8,640,701 B2
(45) Date of Patent: Feb. 4, 2014

(54) CARBON DIOXIDE-BASED BI-LEVEL CPAP CONTROL

(75) Inventor: Joseph B. Richey, II, Chagrin Falls, OH (US)

(73) Assignee: Invacare Corporation, Elyria, OH (US)

( * ) Notice: Subject to any disclaimer, the term of this patent is extended or adjusted under 35 U.S.C. 154(b) by 796 days.

(21) Appl. No.: 11/206,410

(22) Filed: Aug. 18, 2005

(65) Prior Publication Data

US 2005/0279358 A1  Dec. 22, 2005

Related U.S. Application Data

(63) Continuation of application No. 09/967,274, filed on Sep. 27, 2001, now Pat. No. 6,990,980.

(60) Provisional application No. 60/236,123, filed on Sep. 28, 2000.

(51) Int. Cl.
*A61M 16/00* (2006.01)
*A62B 7/00* (2006.01)
*A62B 7/10* (2006.01)

(52) U.S. Cl.
USPC ............ 128/204.26; 128/204.23; 128/204.22; 128/204.18; 128/205.28; 128/205.11; 128/204.21; 128/204.24; 128/205.23; 128/202.22; 128/207.14; 128/207.15

(58) Field of Classification Search
USPC .................. 128/719, 205.23, 202.22, 207.14, 128/207.15, 204.23, 204.22, 204.18, 128/205.28, 204.26, 205.11, 204.21, 204.24
See application file for complete search history.

(56) References Cited

U.S. PATENT DOCUMENTS

| | | | |
|---|---|---|---|
| 3,822,698 A | | 7/1974 | Guy |
| 3,921,628 A | * | 11/1975 | Smythe et al. ........... 128/204.21 |
| 4,011,859 A | | 3/1977 | Frankenberger |
| 4,121,578 A | | 10/1978 | Torzala |
| 4,350,166 A | | 9/1982 | Mobarry |
| 4,506,678 A | | 3/1985 | Russell et al. |
| 4,590,951 A | | 5/1986 | O'Connor |
| 4,648,396 A | | 3/1987 | Raemer |

(Continued)

FOREIGN PATENT DOCUMENTS

| | | |
|---|---|---|
| EP | 164946 | 12/1985 |
| EP | 722747 | 7/1996 |

(Continued)

OTHER PUBLICATIONS

Int'l App. No. PCT/US04/007170, International Preliminary Report on Patentability, 5 pages, report completed Sep. 8, 2005.

(Continued)

*Primary Examiner* — Patricia Bianco
*Assistant Examiner* — Nihir Patel
(74) *Attorney, Agent, or Firm* — Calfee, Halter & Griswold LLP

(57) ABSTRACT

A system and method of providing bi-level CPAP therapy is provided that incorporates an infrared carbon-dioxide sensor to determine whether a patient is inhaling or exhaling. Patient exhalation causes the infrared light to be absorbed, while patient inhalation reduces the presence of carbon-dioxide causes little or no absorption of carbon-dioxide. The level of carbon-dioxide in an associated patient breathing interface is monitored for thresholds that trigger higher CPAP pressure upon inhalation and lower CPAP pressure upon exhalation.

18 Claims, 8 Drawing Sheets

(56) References Cited

U.S. PATENT DOCUMENTS

| | | | |
|---|---|---|---|
| 4,651,729 A | 3/1987 | Rae | |
| 4,655,213 A | 4/1987 | Rapoport et al. | |
| 4,713,558 A | 12/1987 | Russell et al. | |
| 4,728,499 A | 3/1988 | Fehder | |
| 4,773,411 A | 9/1988 | Downs | |
| 4,817,013 A | 3/1989 | Corenman et al. | |
| 4,821,736 A | 4/1989 | Watson | |
| 4,944,310 A | 7/1990 | Sullivan | |
| 4,994,117 A | 2/1991 | Fehder | |
| 5,035,239 A | 7/1991 | Edwards | |
| 5,044,362 A * | 9/1991 | Younes | 128/204.21 |
| 5,065,756 A | 11/1991 | Rapoport | |
| 5,094,235 A * | 3/1992 | Westenskow et al. | 128/204.22 |
| 5,117,819 A | 6/1992 | Servidio et al. | |
| 5,124,129 A | 6/1992 | Riccitelli et al. | |
| 5,134,995 A | 8/1992 | Gruenke et al. | |
| 5,148,802 A | 9/1992 | Sanders et al. | |
| 5,166,075 A | 11/1992 | Fehder | |
| 5,179,002 A | 1/1993 | Fehder | |
| 5,193,544 A * | 3/1993 | Jaffe | 600/323 |
| 5,199,424 A | 4/1993 | Sullivan et al. | |
| 5,203,343 A | 4/1993 | Axe et al. | |
| 5,239,995 A | 8/1993 | Estes et al. | |
| 5,245,995 A | 9/1993 | Sullivan et al. | |
| 5,251,632 A | 10/1993 | Delpy | |
| 5,279,289 A | 1/1994 | Kirk | |
| 5,303,701 A | 4/1994 | Heins et al. | |
| 5,313,937 A | 5/1994 | Zdrojkowski | |
| 5,332,901 A | 7/1994 | Eckles et al. | |
| 5,335,650 A | 8/1994 | Shaffer et al. | |
| 5,335,654 A | 8/1994 | Rapoport | |
| 5,343,878 A | 9/1994 | Scarberry et al. | |
| 5,353,788 A | 10/1994 | Miles | |
| 5,372,130 A | 12/1994 | Stern et al. | |
| 5,394,882 A | 3/1995 | Mawhinney | |
| 5,433,193 A | 7/1995 | Sanders et al. | |
| 5,438,980 A | 8/1995 | Phillips | |
| 5,445,160 A * | 8/1995 | Culver et al. | 600/532 |
| 5,456,249 A | 10/1995 | Kirk | |
| 5,458,137 A | 10/1995 | Axe et al. | |
| 5,490,502 A | 2/1996 | Rapoport et al. | |
| 5,492,113 A | 2/1996 | Estes et al. | |
| 5,503,146 A | 4/1996 | Froehlich et al. | |
| 5,522,382 A | 6/1996 | Sullivan et al. | |
| RE35,295 E | 7/1996 | Estes et al. | |
| 5,535,738 A | 7/1996 | Estes et al. | |
| 5,535,739 A | 7/1996 | Rapoport et al. | |
| 5,537,997 A | 7/1996 | Mechlenburg et al. | |
| 5,538,000 A | 7/1996 | Rudolph | |
| 5,540,219 A | 7/1996 | Mechlenburg et al. | |
| 5,546,933 A | 8/1996 | Rapoport et al. | |
| 5,549,106 A | 8/1996 | Gruenke et al. | |
| 5,551,418 A | 9/1996 | Estes et al. | |
| 5,551,419 A | 9/1996 | Froehlich et al. | |
| 5,558,638 A | 9/1996 | Evers et al. | |
| RE35,339 E | 10/1996 | Rapoport | |
| 5,592,938 A | 1/1997 | Scarberry et al. | |
| 5,598,838 A | 2/1997 | Servidio et al. | |
| 5,630,411 A | 5/1997 | Holscher | |
| 5,632,269 A | 5/1997 | Zdrojkowski | |
| 5,645,054 A | 7/1997 | Cotner et al. | |
| 5,655,522 A | 8/1997 | Mechlenburg et al. | |
| 5,679,884 A | 10/1997 | Kirk | |
| 5,682,878 A | 11/1997 | Ogden | |
| 5,694,923 A | 12/1997 | Hete et al. | |
| 5,701,883 A | 12/1997 | Hete et al. | |
| 5,704,345 A | 1/1998 | Berthon-Jones | |
| 5,715,812 A | 2/1998 | Deighan et al. | |
| 5,738,106 A | 4/1998 | Yamamori et al. | |
| 5,740,795 A | 4/1998 | Brydon | |
| 5,765,563 A | 6/1998 | Vander Schaaf | |
| 5,794,614 A | 8/1998 | Gruenke et al. | |
| 5,794,615 A * | 8/1998 | Estes | 128/204.23 |
| 5,803,065 A | 9/1998 | Zdrojkowski et al. | |
| 5,803,066 A | 9/1998 | Rapoport et al. | |
| 5,823,187 A | 10/1998 | Estes et al. | |
| 5,845,636 A | 12/1998 | Gruenke et al. | |
| 5,865,173 A | 2/1999 | Froehlich | |
| 5,881,717 A | 3/1999 | Isaza | |
| 5,881,723 A | 3/1999 | Wallace et al. | |
| 5,901,704 A | 5/1999 | Estes et al. | |
| 5,904,141 A | 5/1999 | Estes et al. | |
| 5,915,379 A | 6/1999 | Wallace et al. | |
| 5,915,380 A | 6/1999 | Wallace et al. | |
| 5,927,274 A | 7/1999 | Servidio et al. | |
| 5,937,851 A | 8/1999 | Serowski et al. | |
| 5,947,115 A | 9/1999 | Lordo et al. | |
| 5,953,713 A | 9/1999 | Behbehani et al. | |
| 5,954,050 A * | 9/1999 | Christopher | 128/204.23 |
| 5,970,975 A | 10/1999 | Estes et al. | |
| 6,017,315 A | 1/2000 | Starr et al. | |
| 6,024,089 A | 2/2000 | Wallace et al. | |
| 6,026,312 A | 2/2000 | Shemwell et al. | |
| 6,029,660 A | 2/2000 | Calluaud et al. | |
| 6,029,664 A | 2/2000 | Zdrojkowski et al. | |
| 6,029,665 A | 2/2000 | Berthon-Jones | |
| 6,044,843 A | 4/2000 | O'Neil et al. | |
| 6,071,237 A | 6/2000 | Weil et al. | |
| 6,085,747 A | 7/2000 | Axe et al. | |
| 6,091,973 A | 7/2000 | Colla et al. | |
| 6,095,974 A | 8/2000 | Shemwell et al. | |
| 6,099,481 A * | 8/2000 | Daniels et al. | 600/538 |
| 6,102,042 A | 8/2000 | Hete et al. | |
| 6,105,575 A | 8/2000 | Estes et al. | |
| 6,123,074 A | 9/2000 | Hete et al. | |
| 6,123,075 A | 9/2000 | Kirk | |
| 6,135,106 A | 10/2000 | Dirks et al. | |
| 6,138,675 A | 10/2000 | Berthon-Jones | |
| 6,142,952 A | 11/2000 | Behbehani et al. | |
| 6,152,129 A | 11/2000 | Berthon-Jones | |
| 6,155,257 A * | 12/2000 | Lurie et al. | 128/204.23 |
| 6,155,986 A | 12/2000 | Brydon et al. | |
| 6,182,657 B1 | 2/2001 | Brydon et al. | |
| 6,183,423 B1 | 2/2001 | Gaumond et al. | |
| 6,212,435 B1 | 4/2001 | Lattner et al. | |
| 6,213,119 B1 | 4/2001 | Brydon et al. | |
| 6,237,592 B1 | 5/2001 | Surjadi et al. | |
| 6,237,593 B1 | 5/2001 | Brydon | |
| 6,240,921 B1 | 6/2001 | Brydon et al. | |
| 6,253,764 B1 | 7/2001 | Calluaud | |
| 6,257,234 B1 | 7/2001 | Sun | |
| 6,269,811 B1 | 8/2001 | Duff et al. | |
| 6,269,812 B1 | 8/2001 | Wallace et al. | |
| 6,279,569 B1 | 8/2001 | Berthon-Jones | |
| 6,286,508 B1 | 9/2001 | Remmers et al. | |
| 6,299,581 B1 | 10/2001 | Rapoport et al. | |
| 6,302,105 B1 | 10/2001 | Wickham et al. | |
| 6,305,372 B1 | 10/2001 | Servidio | |
| 6,305,373 B1 | 10/2001 | Wallace et al. | |
| 6,305,374 B1 | 10/2001 | Zdrojkowski et al. | |
| 6,347,631 B1 | 2/2002 | Hansen et al. | |
| 6,349,724 B1 | 2/2002 | Burton et al. | |
| 6,357,463 B1 | 3/2002 | Wickham et al. | |
| 6,367,474 B1 * | 4/2002 | Berthon-Jones et al. | 128/204.23 |
| 6,401,713 B1 | 6/2002 | Hill et al. | |
| 6,435,184 B1 | 8/2002 | Ho | |
| 6,443,154 B1 | 9/2002 | Jalde et al. | |
| 6,467,477 B1 | 10/2002 | Frank et al. | |
| 6,516,802 B2 | 2/2003 | Hansen et al. | |
| 6,581,595 B1 * | 6/2003 | Murdock et al. | 128/204.18 |
| 6,609,517 B1 | 8/2003 | Estes et al. | |
| 6,636,021 B2 | 10/2003 | Schenkel et al. | |
| 6,745,770 B2 | 6/2004 | McAuliffe et al. | |
| 6,752,151 B2 | 6/2004 | Hill | |
| 6,766,800 B2 | 7/2004 | Chu et al. | |
| 6,796,305 B1 | 9/2004 | Banner et al. | |
| 6,817,361 B2 | 11/2004 | Berthon-Jones et al. | |
| 6,823,866 B2 | 11/2004 | Jafari et al. | |
| 6,834,646 B2 | 12/2004 | Alon et al. | |
| 6,866,040 B1 | 3/2005 | Bourdon | |
| 6,895,964 B2 | 5/2005 | McAuliffe et al. | |
| 6,932,084 B2 | 8/2005 | Estes et al. | |
| 6,968,842 B1 | 11/2005 | Truschel et al. | |
| 6,990,980 B2 * | 1/2006 | Richey, II | 128/204.26 |

(56) References Cited

U.S. PATENT DOCUMENTS

| | | |
|---|---|---|
| 7,028,688 B1 | 4/2006 | Grove et al. |
| 7,066,173 B2 | 6/2006 | Banner et al. |
| 7,089,936 B2 | 8/2006 | Madaus et al. |
| 7,152,598 B2 | 12/2006 | Morris et al. |
| 7,168,429 B2 | 1/2007 | Matthews et al. |
| 7,621,270 B2 | 11/2009 | Morris et al. |
| 8,020,557 B2 | 9/2011 | Bordewick et al. |
| 8,066,004 B2 | 11/2011 | Morris et al. |
| 8,261,742 B2 | 9/2012 | Strothmann et al. |
| 2001/0004894 A1 | 6/2001 | Bourdon |
| 2001/0015204 A1 | 8/2001 | Hansen et al. |
| 2001/0027791 A1 | 10/2001 | Wallace et al. |
| 2001/0027792 A1 | 10/2001 | Berthon-Jones et al. |
| 2001/0035186 A1 | 11/2001 | Hill |
| 2002/0104536 A1 | 8/2002 | Richey, II |
| 2003/0159695 A1 | 8/2003 | Younes |
| 2004/0035422 A1 | 2/2004 | Truitt et al. |
| 2004/0103896 A1 | 6/2004 | Jafari et al. |
| 2004/0107953 A1 | 6/2004 | Hegge et al. |
| 2004/0123866 A1 | 7/2004 | Berthon-Jones |
| 2004/0187870 A1 | 9/2004 | Matthews et al. |
| 2004/0255943 A1 | 12/2004 | Morris |
| 2005/0016536 A1 | 1/2005 | Rapoport et al. |
| 2005/0020932 A1 | 1/2005 | Haberland et al. |
| 2005/0034724 A1 | 2/2005 | O'Dea |
| 2005/0080461 A1 | 4/2005 | Stahmann et al. |
| 2005/0166922 A1 | 8/2005 | Knepper |
| 2005/0224078 A1 | 10/2005 | Zdrojkowski et al. |
| 2005/0241639 A1 | 11/2005 | Zilberg |
| 2005/0247310 A1 | 11/2005 | Grove et al. |
| 2005/0268913 A1 | 12/2005 | Morris |
| 2006/0000475 A1 | 1/2006 | Matthews et al. |
| 2006/0011200 A1 | 1/2006 | Remmers et al. |
| 2006/0162728 A1 | 7/2006 | Delache et al. |
| 2006/0174889 A1 | 8/2006 | Noble |
| 2006/0180149 A1 | 8/2006 | Matarasso |
| 2007/0000494 A1 | 1/2007 | Banner et al. |
| 2007/0016093 A1 | 1/2007 | Rapoport et al. |
| 2007/0028921 A1 | 2/2007 | Banner et al. |
| 2007/0051371 A1 | 3/2007 | Sullivan et al. |
| 2007/0167843 A1 | 7/2007 | Cho et al. |
| 2008/0060647 A1 | 3/2008 | Messenger et al. |
| 2008/0251079 A1 | 10/2008 | Richey |
| 2009/0050154 A1 | 2/2009 | Strothmann et al. |

FOREIGN PATENT DOCUMENTS

| | | |
|---|---|---|
| JP | 7-096035 | 4/1995 |
| JP | 10-505765 | 6/1998 |
| JP | 3090468 | 7/2000 |
| JP | 2001-000547 | 1/2001 |
| WO | 90/14121 | 11/1990 |
| WO | 02/26283 | 4/2002 |
| WO | 02/26287 | 4/2002 |
| WO | 2005/004780 | 1/2005 |
| WO | 2005/028009 | 3/2005 |
| WO | 2005/063323 | 7/2005 |
| WO | 2006/009939 | 1/2006 |
| WO | 2008/127986 | 10/2008 |

OTHER PUBLICATIONS

Int'l App. No. PCT/US04/007170, International Search Report, 2 pages, mailed Jan. 27, 2005.
Int'l App. No. PCT/US04/007170, Written Opinion of the International Searching Authority, 5 pages, mailed Jan. 27, 2005.
Lankford, Got Compliance?, ResMed PowerPoint presentation, 34 pages.
Leung et al., Sleep Apnea and Cardiovascular Disease, Am J Respir Crit Care Med, vol. 164, pp. 2147-2165, 2001.
Int'l Pat. App. No. PCT/US01/30768, International Search Report, mailed May 31, 2002.
Int'l Pat. App. No. PCT/US01/30768, Written Opinion, mailed Dec. 12, 2002.
Int'l Pat. App. No. PCT/US01/30768, International Preliminary Examination Report, completed Apr. 15, 2003.
U.S. Appl. No. 09/967,274, Non-final Office Action, mailed Apr. 23, 2003.
U.S. Appl. No. 09/967,274, Non-final Office Action, mailed Jan. 14, 2004.
U.S. Appl. No. 09/967,274, Non-final Office Action, mailed Jul. 27, 2004.
U.S. Appl. No. 09/967,274, Final Office Action, mailed Jan. 25, 2005.
U.S. Appl. No. 09/967,274, Notice of Allowance and Fee(s) Due and Notice of Allowability with Examiner's Statement of Reasons for Allowance, mailed Jul. 11, 2005.
Communication Issued for European Application No. 01973647.9, dated Aug. 13, 2009, forwarding Supplemental Search Report, dated Jul. 27, 2009.
Liesching et al., "Evaluation of the Accuracy of SNAP Technology Sleep Sonography in Detecting Obstructive Sleep Apnea in Adults Compared to Standard Polysomnography, Chest—The Cardiopulmonary and Critical Care Journal", vol. 125, No. 3, pp. 886-891, Mar. 2004.
Nellcor Puritan Bennett, Inc., Breeze SleepGear and DreamSeal Assembly Coding Matrix, A.d. 0426v2-0304, ST03700, 2 pgs. Copyright 2004.
Nellcor Puritan Bennett, Inc., Breeze SleepGear Users Guide, pp. 3, 4, 6 and 13, copyright 2004.
Nellcor Puritan Bennett, Inc., Dreamfit Nasal Mask, www.puritanbennett.com/prod/Product.aspx?S1=SPT&S2=CPI&id=284, 2 pgs. Printed Oct. 2, 2006, copyright 2006.
Penzel et al., "Systemic comparison of different algorithms for apnea detection based on electrocardiogram recordsings", Medical & Biological Engineering & Computing, vol. 40, pp. 402-407 (2002).
Researchers create DNA-based nanosensors, Small Times Magazine, 1 pg, Sep. 16, 2005.
ResMed, S8 AutoSet Vantage—AutoSet Technology, resmed.com/portal/site/ResMedUS/?vgnCld=9ec827e4bd475010vbnVCMServerc6 . . . , printed on Jun. 24, 2006, 3 pgs., copyright 2000-2006, last updated Sep. 12, 2005.
Ryan et al., Periodicity of Obstructive Sleep Apnea in Patients with and without heart failure, Chest Journal, vol. 127, No. 2, pp. 536-542, Feb. 2005.
Tamisier et al., "Expiratory Changes in Pressure: Flow Ratio During Sleep in Patients with Sleep-disordered breathing", Sleep, vol. 27, No. 2, pp. 240-248, 2004.
Tyco Healthcare UK Ltd., Breeze Sleep Gear CPAP Interface System, A.b. 1751-0504, ST00900, 2 pgs. Copyright 2004.
Tyco Healthcare UK Ltd., Breeze SleepGear CPAP Interface System, C-AD-Breeze/GB, 4 pgs., copyright 2004, Jul. 2004.
Tyco Healthcare UK Ltd., New Easy-to-Fit CPAP Interface [dreamfit nasalmask], A.ae 2175v2-0905, ST06604, 2 pgs., copyright 2005, Sep. 2005.
Response to Communication for European Application No. 01973647.9, dated Dec. 2, 2009.
Response from U.S. Appl. No. 11/519,532 dated Dec. 1, 2010.
Office action from Japanese Application No. 2007-516811 dated Sep. 29, 2010.
Declaration of Non-Establishment of International Search Report and Written Opinion from PCT/US05/21638 dated Sep. 23, 2005.
International Search Report from PCT/US08/59915 dated Sep. 17, 2008.
Written Opinion from PCT/US08/59915 dated Sep. 17, 2008.
International Search Report and Written Opinion from PCT/US08/74194 dated Dec. 3, 2008.
Response from U.S. Appl. No. 09/967,274 dated Sep. 23, 2003.
Response from U.S. Appl. No. 09/967,274 dated Apr. 13, 2004.
Response from U.S. Appl. No. 09/967,274 dated Oct. 27, 2004.
Response from U.S. Appl. No. 09/967,274 dated May 23, 2005.
Response from U.S. Appl. No. 10/601,720 dated Mar. 28, 2005.
Response from U.S. Appl. No. 10/601,720 dated Nov. 21, 2005.
Response from U.S. Appl. No. 10/601,720 dated Jun. 7, 2006.
Office action from U.S. Appl. No. 11/157,089 dated Feb. 23, 2009.
Response from U.S. Appl. No. 11/157,089 dated May 26, 2009.
Notice of Allowance from U.S. Appl. No. 11/157,089 dated Jul. 15, 2009.

(56) References Cited

OTHER PUBLICATIONS

Supplemental Notice of Allowance from U.S. Appl. No. 11/157,089 dated Aug. 24, 2009.
Office action from U.S. Appl. No. 11/519,532 dated Nov. 16, 2009.
Response from U.S. Appl. No. 11/519,532 dated Apr. 6, 2010.
Office action from U.S. Appl. No. 11/519,532 dated Jul. 1, 2010.
Office action from Chinese application No. 200580028591.2 dated Feb. 6, 2009.
Response from Chinese application No. 200580028591.2 dated Jun. 19, 2009.
Office action from Chinese application No. 200580028591.2 dated Jul. 24, 2009.
Response from Chinese application No. 200580028591.2 dated Dec. 7, 2009.
Office action from Chinese application No. 200580028591.2 dated Jan. 8, 2010.
Response from Chinese application No. 200580028591.2 dated Mar. 19, 2010.
Office action from Chinese application No. 200580028591.2 dated Apr. 28, 2010.
Response from Chinese application No. 200580028591.2 dated Jun. 16, 2010.
Communication from EP Application No. 04719190.3 dated Apr. 7, 2009.
Response to EP Communication from Application No. 04719190.3 dated Jun. 16, 2009.
Communication from EP Application No. 04719190.3 dated Nov. 12, 2009.
Response to EP Communication for Application No. 04719190.3 dated May 12, 2010.
Communication from EP Application No. 05766008.6 dated Nov. 5, 2009.
Response to EP Communication from Application No. 05766008.6 dted Mar. 8, 2010.
Belozeroff et al., "Effects of CPAP therapy on cardiovascular variability in obstructive sleep apnea: a closed-loop analysis", Am J Physiol—Heart Circ Physiol, vol. 282, pp. H110-H121, Jan. 2002.
Bliss et al., "Performance of Auto-Titrating CPAP Devices in a Simulation of Varied Patient Breathing", AARC International Congress, San Antonio, TX, 6 pgs., Dec. 2001.
Cairo et al., "Mosby's Respiratory Care Equipment", Chapter 14—Sleep Diagnostics, pp. 682-698, 7th ed., Jul. 31, 2003.
Farre et al., "Response of Automatic Continuous Positive Airway Pressure Devices to Different Sleep Breathing Patterns—A Bench Study", Am. J. Respir. Crit Care Med, vol. 166, pp. 469-473, 2002.
Heitman et al. "Validation of nasal pressure for the identificaton of apneas/hypopneas during sleep", Am J Respir Crit Care Med, vol. 166, pp. 386-391, 2002.
Invacare Corp., Owner's Manual, Polaris/Polaris LT Nasal CPAP System, 20 pgs. Copyright 2002, Ref F, Jul. 2002.
Office action from U.S. Appl. No. 12/197,692 dated Aug. 17, 2011.
Office action from U.S. Appl. No. 11/519,532 dated Mar. 7, 2011.
Response from U.S. Appl. No. 11/519,532 dated Aug. 5, 2011.
Office action from EP Application No. 04719190-3 dated Apr. 1, 2011.
Response from EP Application No. 04719190-3 dated May 13, 2011.
Mosbacker, "Circulatory System", pp. 1-3, Art Today, Utah Education Network, www.uen.org/utahlink/activities/view_activity.cgi?activity_id=3043 printed Feb. 24, 2011.
Office action from U.S. Appl. No. 11/519,532 dated Oct. 11, 2011.
Issue Notification from U.S. Appl. No. 12/623,994 dated Nov. 29, 2011.
Office action from Canadian application No. 2,530,523 dated Dec. 1, 2011.
Office action from Chinese application No. 201010522527.2 dated Oct. 19, 2011.
Office action from EP Application No. 04719190-3 dated Nov. 4, 2011.
Exam Report from EP Application No. 05766008.6 dated Oct. 17, 2011.
Notice of Allowance for U.S. Appl. No. 12/623,994 dated Sep. 22, 2011.
Office action from U.S. Appl. No. 12/100,931 dated Sep. 11, 2012.
Response from U.S. Appl. No. 12/197,692 dated Feb. 17, 2012.
Notice of Allowance from U.S. Appl. No. 12/197,692 dated Mar. 9, 2012.
First Office Action from Chinese Application No. 200880020253.8 dated Jan. 18, 2012.
Response to First Office Action from Chinese Application No. 201010522527.2 dated Feb. 10, 2012.
Office action from Chinese application No. 201010522527.2 dated Feb. 20, 2012.
Response to Office Action from Chinese application No. 201010522527.5 dated Feb. 27, 2012.
Response to EP Communication No. 05766008.6 dated Mar. 16, 2012.
Notice of Allowance from U.S. Appl. No. 12/197,692 dated May 11, 2012.
Response to Office Action from EP Application No. 04719190.3 dated May 3, 2012.
First Examination Report from AU Application No. 2008240290 dated Jun. 12, 2012.
Mallinckrodt, Inc., Break free to Breeze and DreamSeal, Puritan-Bennett SleepGear, MS-AC/Breeze/GB, 6 pages, Copyright 2000.
Portier et al., Evaluation of Home versus Laboratory Polysomnography in the Diagnosis of Sleep Apnea Syndrome, Am J Respir Crit Care Med, vol. 162, pp. 814-818, 2000.
U.S. Appl. No. 10/601,720, Non-final Office Action, 6 pages, mailed Jun. 21, 2005.
U.S. Appl. No. 10/601,720, Non-final Office Action, 7 pages, mailed Jan. 6, 2005.
U.S. Appl. No. 10/601,720, Non-final Office Action, 8 pages, mailed Feb. 7, 2006.
U.S. Appl. No. 10/601,720, Notice of Allowance and Fee(s) Due and Notice of Allowability, 4 pages, mailed Aug. 8, 2006.
First Office Action from Canadian application No. 2,571,164 dated Dec. 12, 2012.
Amendment from U.S. Appl. No. 12/100,931 dated Jan. 11, 2013.
Further Office action from Canadian application No. 2,530,523 dated Feb. 20, 2013.

\* cited by examiner

CARBON DIOXIDE-BASED BI-LEVEL CPAP CONTROL

CROSS-REFERENCE TO RELATED APPLICATIONS

This is a continuation of co-pending U.S. patent application Ser. No. 09/967,274 filed Sep. 27, 2001 and entitled CARBON DIOXIDE-BASED BI-LEVEL CPAP CONTROL, the entire disclosure of which is fully incorporated herein by reference.

This patent application is related to provisional application Ser. No. 60/236,123, titled "Carbon Dioxide-Based Bi-Level CPAP Control," which is hereby fully incorporated by reference.

FIELD OF THE INVENTION

The invention relates generally to the administration of constant positive airway pressure (CPAP) to treat obstructive sleep apnea, and more particularly, to methods and apparatuses for administering a higher CPAP upon inhalation and a lower CPAP upon exhalation.

BACKGROUND OF THE INVENTION

Obstructive sleep apnea is an airway breathing disorder caused by relaxation of the muscles of the upper airway to the point where the upper airway collapses or becomes obstructed by these same muscles. It is known that obstructive sleep apnea can be treated through the application of pressurized air to the nasal passages of a patient. The application of pressurized air forms a pneumatic splint in the upper airway of the patient thereby preventing the collapse or obstruction thereof.

Within the treatment of obstructive sleep apnea, there are several known CPAP regimens including, for example, mono-level CPAP and bi-level CPAP. Mono-level CPAP involves the constant application of a single therapeutic CPAP level. That is, through the entire breathing cycle, a single therapeutic positive air pressure is delivered to the patient. While such a regimen is successful in treating obstructive sleep apnea, some patients experience discomfort when exhaling because of the level of positive air pressure being delivered to their airways during exhalation.

In response to this discomfort, bi-level CPAP regimens were developed. Bi-level CPAP involves delivering a higher therapeutic CPAP during inhalation and a lower therapeutic CPAP during exhalation. The higher therapeutic CPAP level is commonly known as inspiratory positive airway pressure or "IPAP." The lower therapeutic CPAP level is commonly known as expiratory positive airway pressure or "EPAP." Since the EPAP is lower than the IPAP, the patient needs to do less work during exhalation to exhale and thus experiences less discomfort, compared to the mono-level CPAP regimen.

However, the development of bi-level CPAP significantly increased the sophistication of CPAP devices because the devices must accurately determine when the patient is inhaling and exhaling and to properly coordinate the IPAP and EPAP levels thereto. One approach is to determine the instantaneous and average flow rates of air being delivered to the patient and then to compare the two to determine whether a patient was inhaling or exhaling. If the instantaneous flow rate is greater than the average flow rate, the patient is deemed to be inhaling. If the instantaneous flow rate is less than the average flow rate, the patient is deemed to be exhaling. However, using the instantaneous and average flow rates of the air being delivered to the patient has several disadvantages including accuracy and response time. In this regard, the flow of air is generally turbulent and therefore difficult to measure accurately. Additionally, leakages caused by loose fitting patient breathing interfaces such as, for example, nasal and mouth masks, contribute to the difficulty of determining accurate air flow rates. Closely connected thereto, the turbulent flow and difficulty of accurate measurement necessarily cause a slow response time in changing between IPAP and EPAP levels. Hence, a bi-level CPAP device that does not suffer from these deficiencies is highly desirable.

SUMMARY OF THE INVENTION

According to one embodiment of the present invention, a carbon-dioxide sensor is used to determine whether a patient undergoing bi-level CPAP treatment for obstructive sleep apnea is inhaling or exhaling. The carbon-dioxide sensor uses infrared light to determine the presence or absence of carbon-dioxide in a patient breathing interface such as, for example, a nasal and mouth mask, worn by the patient. In this regard, the carbon-dioxide sensor includes, for example, an infrared light emitter and detector separated by an air gap. Patient exhalation results in carbon-dioxide being present in the air gap. This causes less infrared light to be transmitted to the detector due to the carbon-dioxide absorbing a portion of the infrared light. Conversely, patient inhalation results in little or no carbon-dioxide being present in the air gap. This causes more infrared light to be transmitted to the detector because there is little or no carbon-dioxide present to absorb the infrared light. Through such detection, the logic of the present invention coordinates the IPAP and EPAP levels to provide the patient with a comfortable bi-level CPAP regimen.

In a first embodiment, the level of carbon-dioxide is monitored to determine whether it is above or below a threshold parameter or value. If the level of carbon dioxide is above the threshold, the patient is exhaling and an EPAP level is provided. If the level of carbon-dioxide is below the threshold, the patient is inhaling and an IPAP level is provided to the patient. Hence, the same threshold is used once to trigger EPAP and again to trigger IPAP.

In a second embodiment, monostable timer control is used to trigger the EPAP and IPAP. In this regard, the monostable timer is trigger to its fixed duration on state when the level of carbon-dioxide is decreasing and falls below a threshold parameter or value. Once this happens, the patient is inhaling and an IPAP level is provided. Upon expiration of the monostable timer's fixed duration on state, patient exhalation is assumed and an EPAP level is provided until the monostable timer is once again triggered.

It is therefore an object of the present invention to provide a system and method of providing a higher positive airway pressure breathing gas during patient inhalation and a lower positive airway pressure breathing gas during patient exhalation.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to example the principles of this invention.

DETAILED DESCRIPTION OF THE ILLUSTRATED EMBODIMENT

Figure 1:
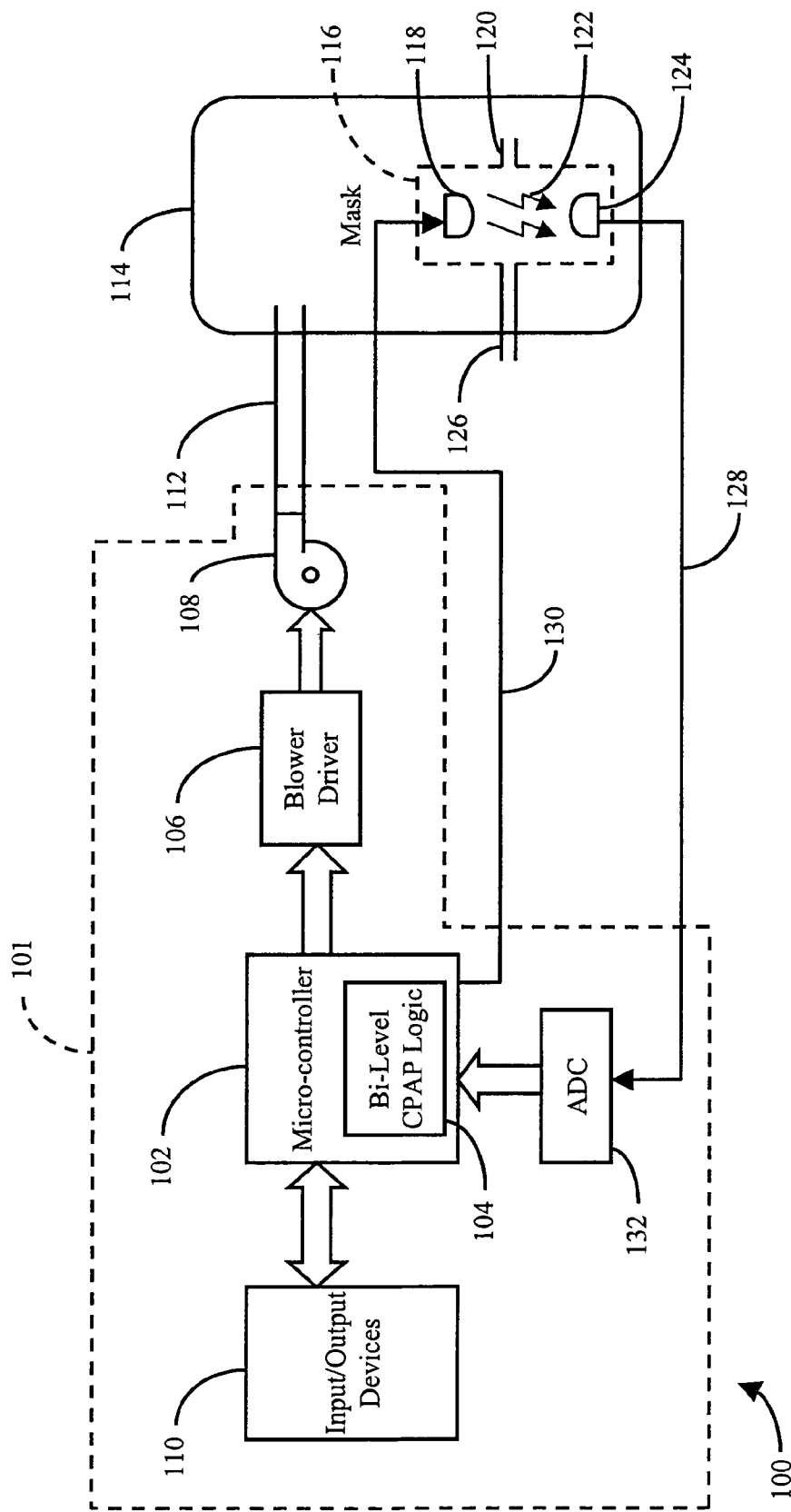
FIG. 1 is a functional block diagram of a system of the present invention having a carbon-dioxide sensor integral with a nasal mask.

Illustrated in FIG. 1 is a first bi-level CPAP system 100 of the present invention. The system has a bi-level CPAP apparatus 101 and a patient breathing interface 114. The bi-level CPAP apparatus 101 has a micro-controller 102 with associated bi-level CPAP logic 104. The micro-controller 102 interfaces with a plurality of components including input/output devices 110, analog-to-digital converter (ADC) 132, and blower driver 106. Input/Output devices 110 include, for example, controls that allow a clinician or doctor to set the IPAP and EPAP levels in micro-controller 102 and in bi-level CPAP logic 104. Blower driver 106 interfaces with and drives blower 108 through a range of variable speeds that result in a range of variable air pressures that define the IPAP and EPAP levels. The blower 108 preferably has a motor and a fan and is driven by a pulse-width modulated (PWM) signal wherein the pulse width or duty cycle defines the variable speed and pressure of the blower. Alternatively, an adjustable valve can be used to vary the bi-level CPAP pressure between IPAP and CPAP levels such as described in U.S. Pat. No. 5,433,193, which is hereby fully incorporated by reference.

System 100 also includes a patient breathing interface 114, such as a mask, that is worn by a patient that is to receive bi-level CPAP therapy. Patient breathing interface 114 is connected to blower 108 through supply tubing 112, which supplies the IPAP and EPAP levels to the patient from the CPAP apparatus 101. In the present embodiment, patient breathing interface 114 has a carbon-dioxide sensor 116 integral therewith for detecting the presence of carbon-dioxide in the mask.

Carbon-dioxide sensor 116 preferably includes an infrared light emitter 118 and an infrared light detector 124. Infrared light emitter 118 is preferably an incandescent light source emitting light in the infrared frequency range. However, infrared light emitting diodes can also be employed. Infrared light detector 124 is of conventional design. Infrared light emitter 118 is separated from infrared light detector 124 by an air gap such that infrared light 122 emitted from emitter 118 is directed across the air gap and towards detector 124.

In this regard, it is known that carbon-dioxide absorbs light in the infrared energy spectrum. See, for example, U.S. Pat. No. 4,648,396 to Raemer, which is hereby fully incorporated by reference. Hence, when a gas having carbon-dioxide is present in the air gap between infrared light emitter 118 and detector 124, less infrared light is transmitted to detector 124 than if no carbon-dioxide was present in the air gap. This is indicated by the output (i.e., signal 128) of detector 124 falling to a level indicative of the amount of infrared light that is not being absorbed by the carbon-dioxide. In this manner, carbon-dioxide sensor 116 senses the amount of carbon-dioxide present.

Carbon-dioxide sensor 116 further includes an input port 120 and in output port 126. Input port 120 allows gases present in patient breathing interface 114 to pass into carbon-dioxide sensor 116 and between the air gap separating infrared light emitter 118 and detector 124 for carbon-dioxide detection. Output port 126 allows venting of the gases in carbon-dioxide sensor 116 to the outside atmosphere. Configured as such, carbon-dioxide sensor 116 also performs a venting function provided for by most conventional patient breathing interfaces.

As shown in FIG. 1, bi-level CPAP apparatus 101 is in circuit communication with infrared light emitter 118 and detector 124. More particularly, micro-controller 102 drives infrared light emitter 118 on and off through signal line 130 and conventional drive circuitry (not shown). Micro-controller 102 also reads the output of infrared light detector 124 through signal line 128 and ADC 132. In this manner, micro-controller 102 controls carbon-dioxide sensor 116 and reads its output signal to thereby determine the presence or absence of carbon-dioxide in patient breathing interface 114. As will be described in more detail in connection with the logic of FIG. 4, the presence of carbon-dioxide indicates that a wearer of patient breathing interface 114 is exhaling and the absence of carbon-dioxide indicates that the wearer is inhaling. By knowing when the patient is inhaling and exhaling, micro-controller 102 and bi-level CPAP logic 104 can vary the air pressure delivered by blower 108 to the proper IPAP and EPAP levels set by the clinician or doctor.

Figure 2:
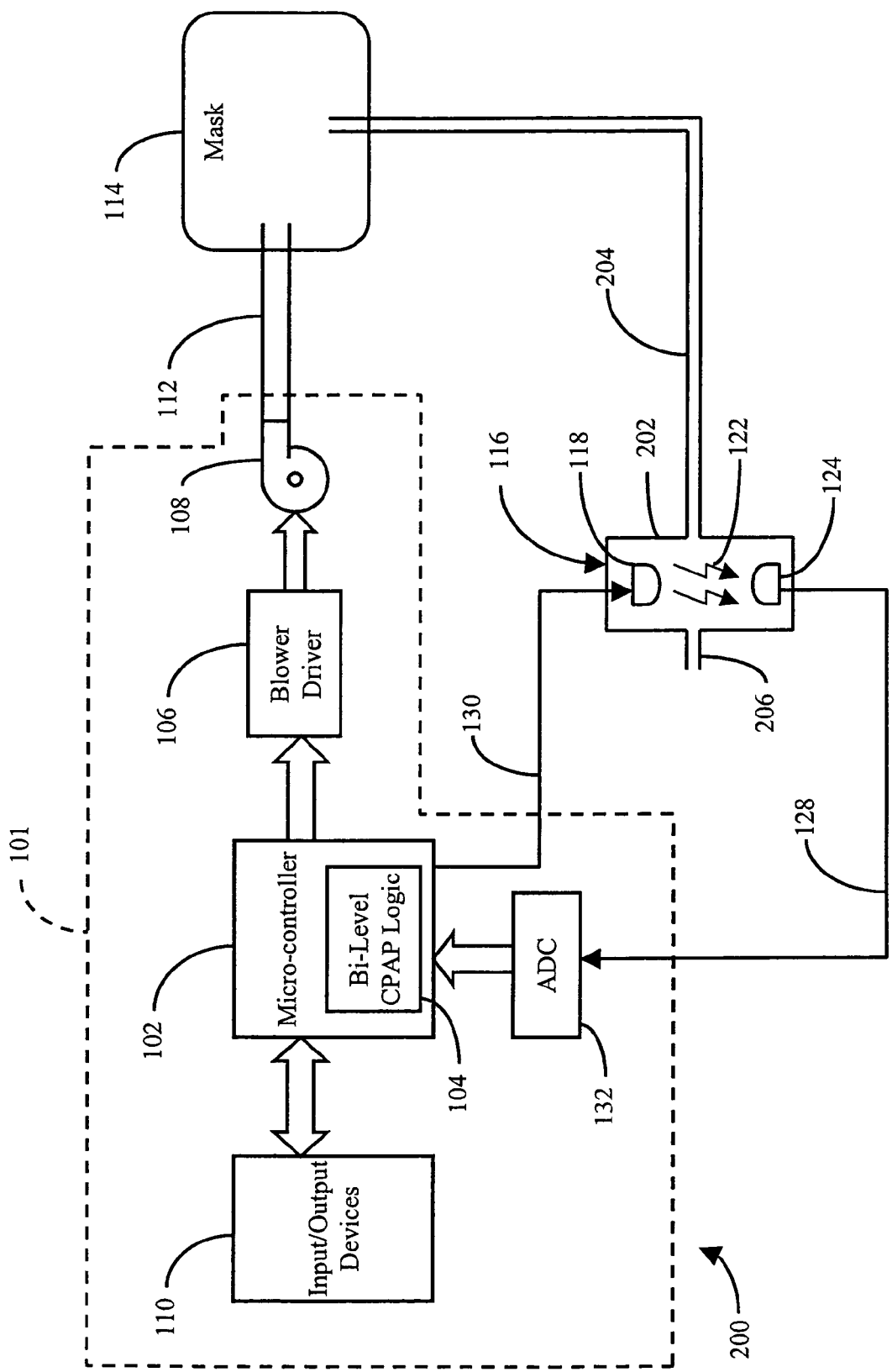
FIG. 2 is a functional block diagram of a system of the present invention having a carbon-dioxide sensor external to a nasal mask.

FIG. 2 illustrates a bi-level CPAP system 200 that is similar system 100 of FIG. 1, except that carbon-dioxide sensor 116 is external to the patient breathing interface 114. In system 200, carbon-dioxide sensor 116 has a housing 202 that is connected to patient breathing interface 114 through tubing 204. Tubing 204 functions as the input port to carbon-dioxide sensor 116 by delivering gases thereto from patient breathing interface 114. Housing 202 also includes an output port 206 that allows venting of the gases in carbon-dioxide sensor 116 to the outside atmosphere.

Figure 3:
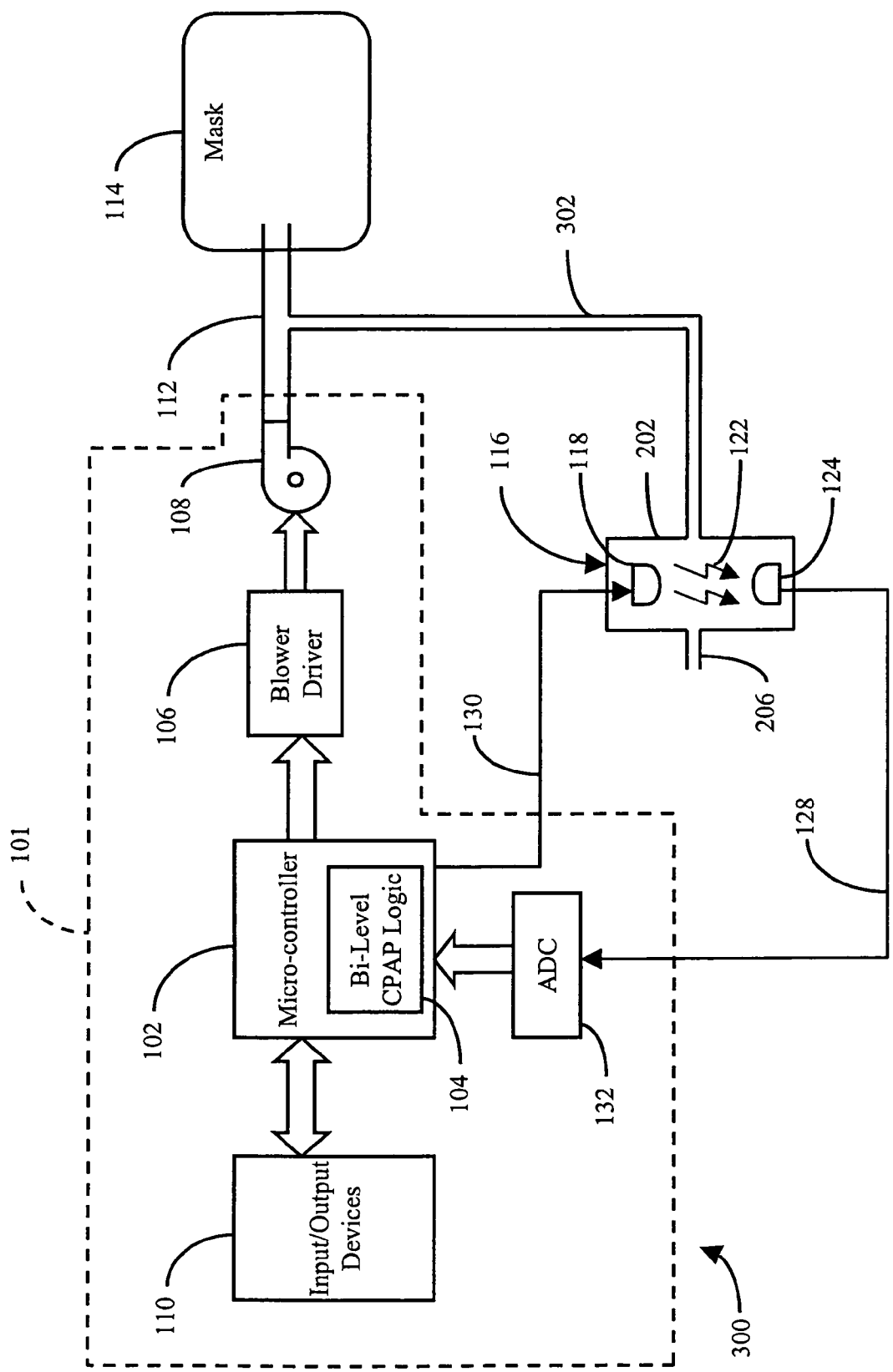
FIG. 3 is a functional block diagram of a system of the present invention having a carbon-dioxide sensor external to a nasal mask and indirectly connected thereto.

FIG. 3 illustrates a bi-level CPAP system 300 that is similar to system 200 of FIG. 2, except that carbon-dioxide sensor 116 is not directly connected to patient breathing interface 114. Rather, carbon-dioxide detector 116 is indirectly connected to patient breathing interface 114 via sensor tubing 302 and supply tubing 112. In all other aspects, systems 200 and 300 are similar to system 100 of FIG. 1.

Figure 4:
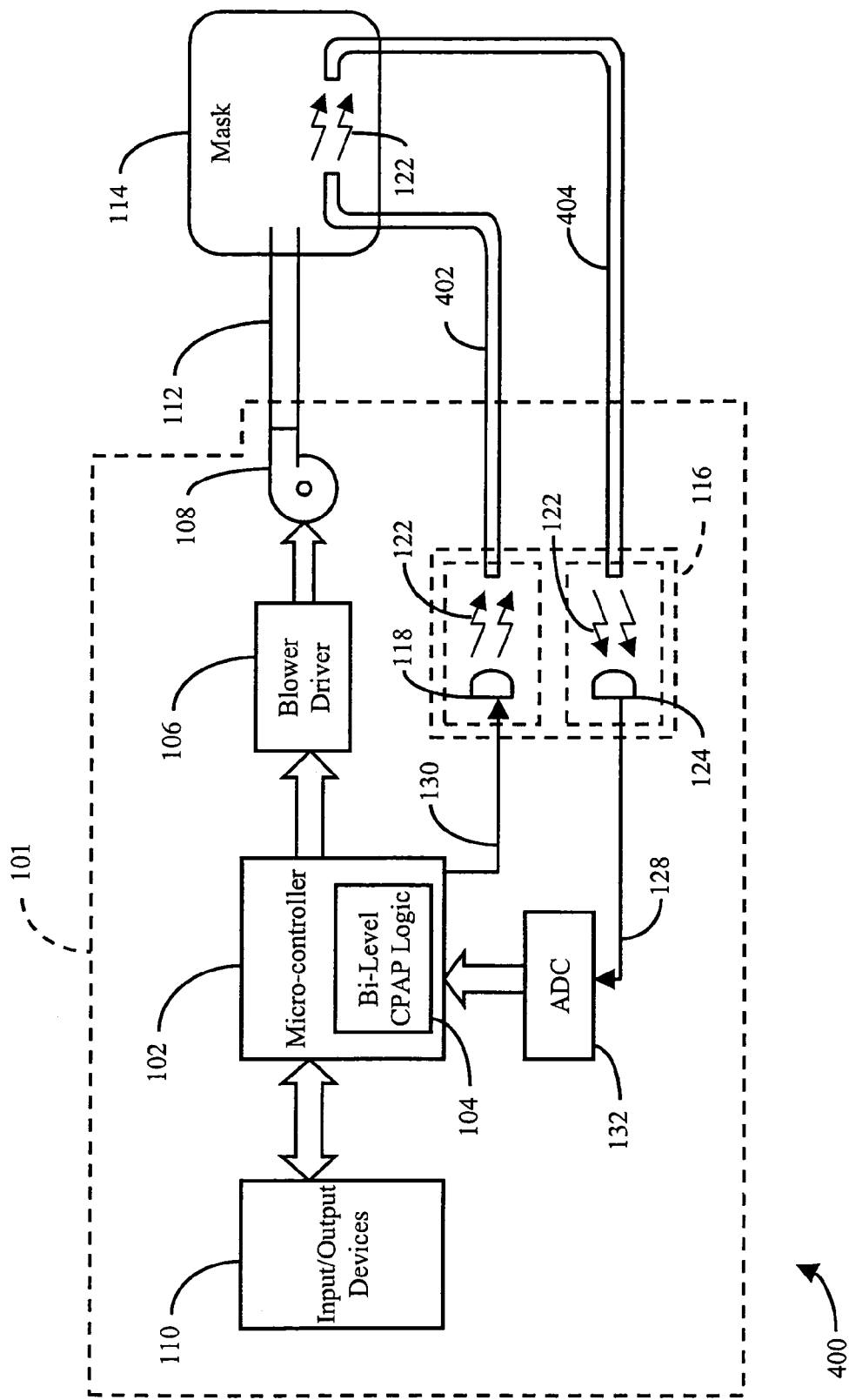
FIG. 4 is a functional block diagram of a system of the present invention having a carbon-dioxide sensor that is connected to a nasal mask with optical fibers.

Illustrated in FIG. 4 is a system 400 of the present invention that employs optical fibers to carry infrared light to and from patient breathing interface 114. In particular, carbon-dioxide sensor 116 is external to patient breathing interface 114 and preferably located within bi-level CPAP apparatus 101. A plurality of optical fibers carry infrared light from infrared light emitter 118 to patient breathing interface 114 and back to infrared light detector 124. Within patient breathing interface 114, optical fibers 402 and 404 are terminated such that infrared light exiting optical fiber 402 is ultimately directed across an air gap and to optical fiber 404 for return to infrared light detector 124. The fiber optic terminations and air gap are preferably disposed across one or more of the venting mechanisms (i.e., one or more holes or vents) of patient breathing interface 114. In this regard, exhaled gases that are normally vented through such mechanisms can be monitored by carbon-dioxide sensor 116. It should also be noted in FIG. 4 that optical fibers 402 and 404 can be connected in a similar manner to supply tube 112 rather patient breathing interface 114. Configured as such, system 400 is particularly advantageous because it does not require the use of additional tubing and allows the carbon-dioxide sensor 116 to be housed with bi-level CPAP apparatus 101.

Figure 5:
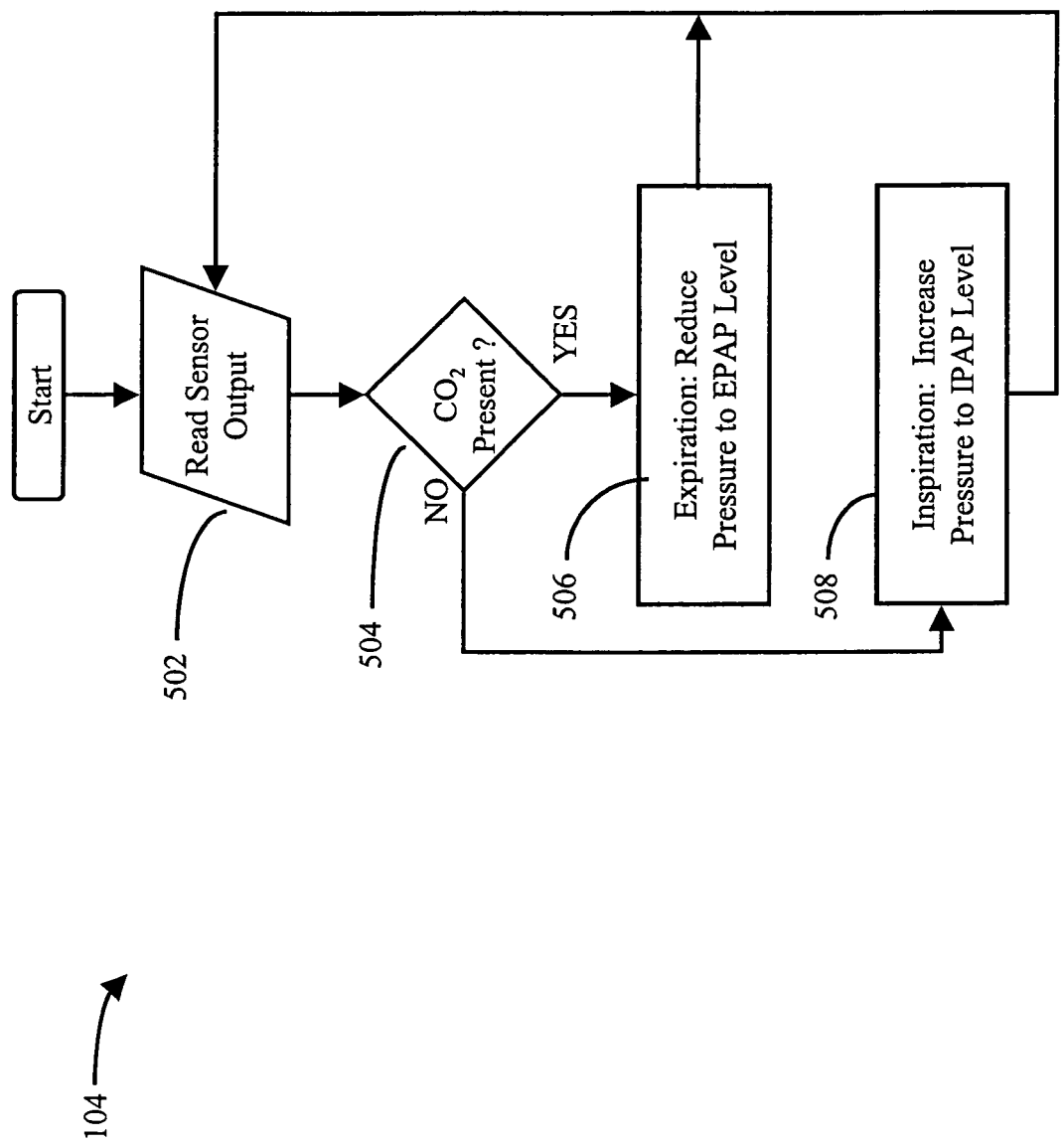
FIG. 5 is a flow chart of the bi-level CPAP logic of the present invention.

Referring now to FIG. 5, a flowchart illustrating the bi-level CPAP logic 104 of the present invention is shown. The bi-level CPAP logic 104 is executed by micro-controller 102. The logic starts in step 502 where micro-controller 102 reads the value of carbon-dioxide sensor 116 output signal 128.

In step 504, the logic determines if carbon-dioxide is present in the patient breathing interface by comparing the value of the sensor output signal 128 against a threshold parameter or value. The threshold parameter or value is preferably a carbon-dioxide level within the patient breathing interface that is representative of the state of exhalation by the patient. If the value of sensor output signal 128 is less than the threshold parameter, then carbon-dioxide is sufficiently present and, therefore, the patient is exhaling. In this scenario, the logic advances to step 506. In step 506, micro-controller 102 directs blower 108 to reduce its output pressure to EPAP level by preferably decreasing the duty cycle of the blower's PWM driving signal. After step 506, the logic loops back to step 502 and once again reads the value of carbon-dioxide sensor 116 output signal 128.

However, if in step 504 the value of sensor output signal 128 is greater than the threshold parameter, then carbon-dioxide is deemed to be sufficiently absent and, therefore, the patient is inhaling. In this scenario, the logic advances to step 508 where the micro-controller 102 directs blower 108 to increase its output pressure to IPAP level by preferably increasing the duty cycle of the blower's PWM driving signal. After step 508, the logic loops back to step 502 and once gain reads the carbon-dioxide sensor 116 output signal 128 to determine the appropriate CPAP level (i.e., IPAP or EPAP). In this manner, micro-controller 102 reads carbon-dioxide sensor 116 to determine the presence and absence of carbon-dioxide and to properly coordinate the IPAP and EPAP levels with the patient's inspiratory and expiratory cycles.

Figure 6:
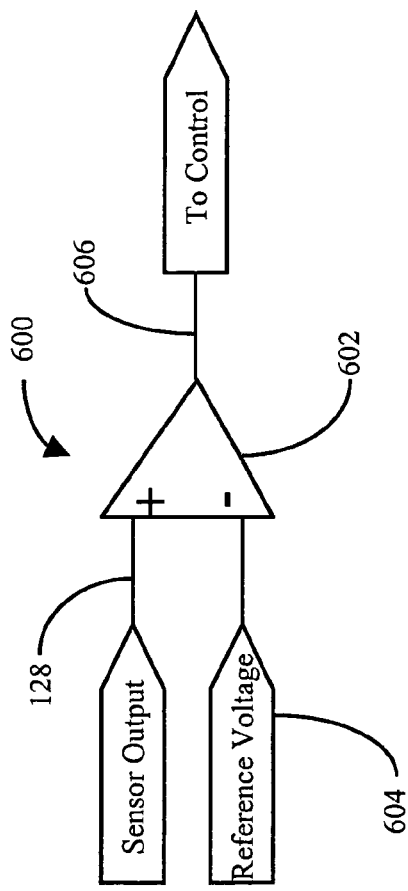
FIG. 6 is a schematic diagram of a comparator circuit of the present invention.

Referring now to FIG. 6, an analog comparator circuit 600 is shown that can be used as an alternative to ADC 132. The circuit 600 preferably includes an operational amplifier 602 that receives sensor output signal 128 at its positive input terminal and a reference or threshold voltage signal 604 at its negative input terminal. The output 606 of operational amplifier 602 is preferably connected to micro-controller 102 or other CPAP control circuitry.

Figure 7:
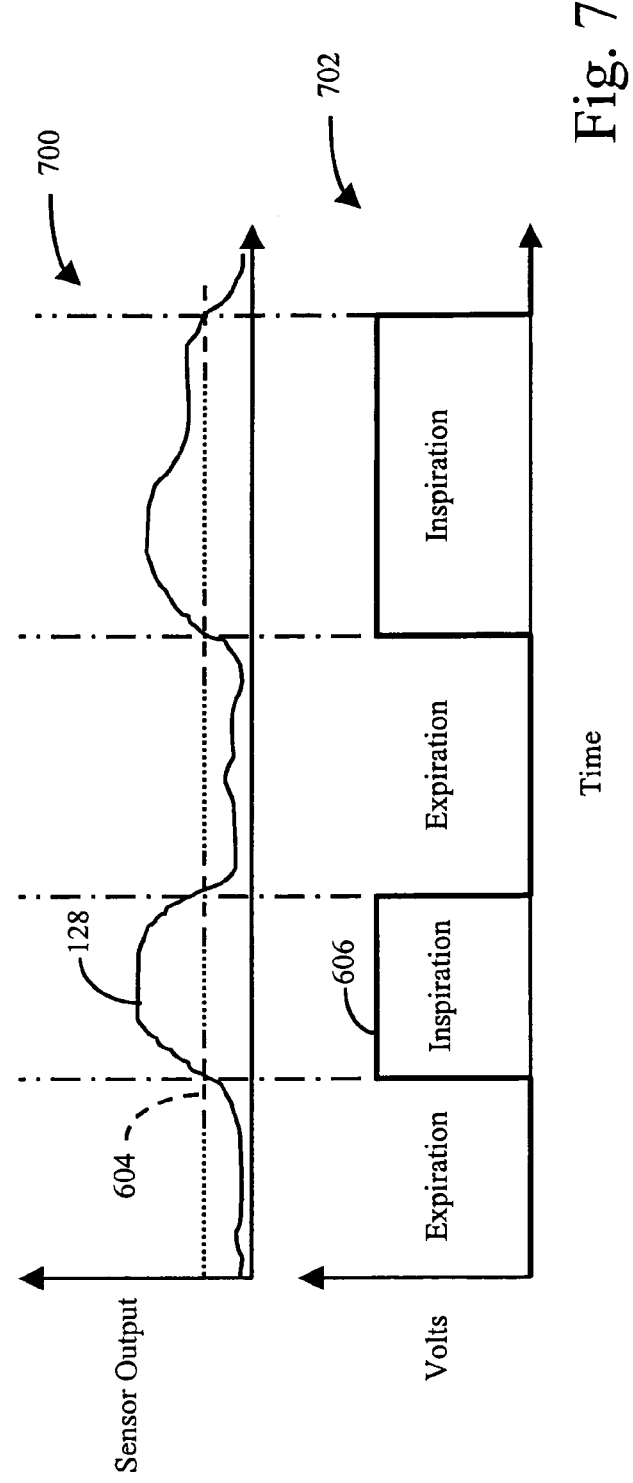
FIG. 7 illustrates graphs of the input and output signals of the comparator circuit of FIG. 5.

As shown in graphs 700 and 702 of FIG. 7, whenever sensor output signal 128 is greater than reference or threshold parameter, as represented by voltage signal 604, comparator 500 output signal 606 preferably increases to a positive voltage level. This indicates that carbon-dioxide is sufficiently absent so as to signify that the patient is inhaling and that blower 108 should provide the prescribed IPAP level. Whenever sensor output signal 128 is less than the reference or threshold parameter 604, comparator 600 output signal 606 preferably falls to a lower voltage level. This indicates that carbon-dioxide is sufficiently present so as to signify that the patient is exhaling and that blower 108 should provide the prescribed EPAP level. Alternately, threshold parameter 604 can be in the form of first and second threshold parameter: one for inhalation detection and one for exhalation detection. This configuration compensates for potential differences in carbon-dioxide inhalation and exhalation thresholds.

Figure 8:
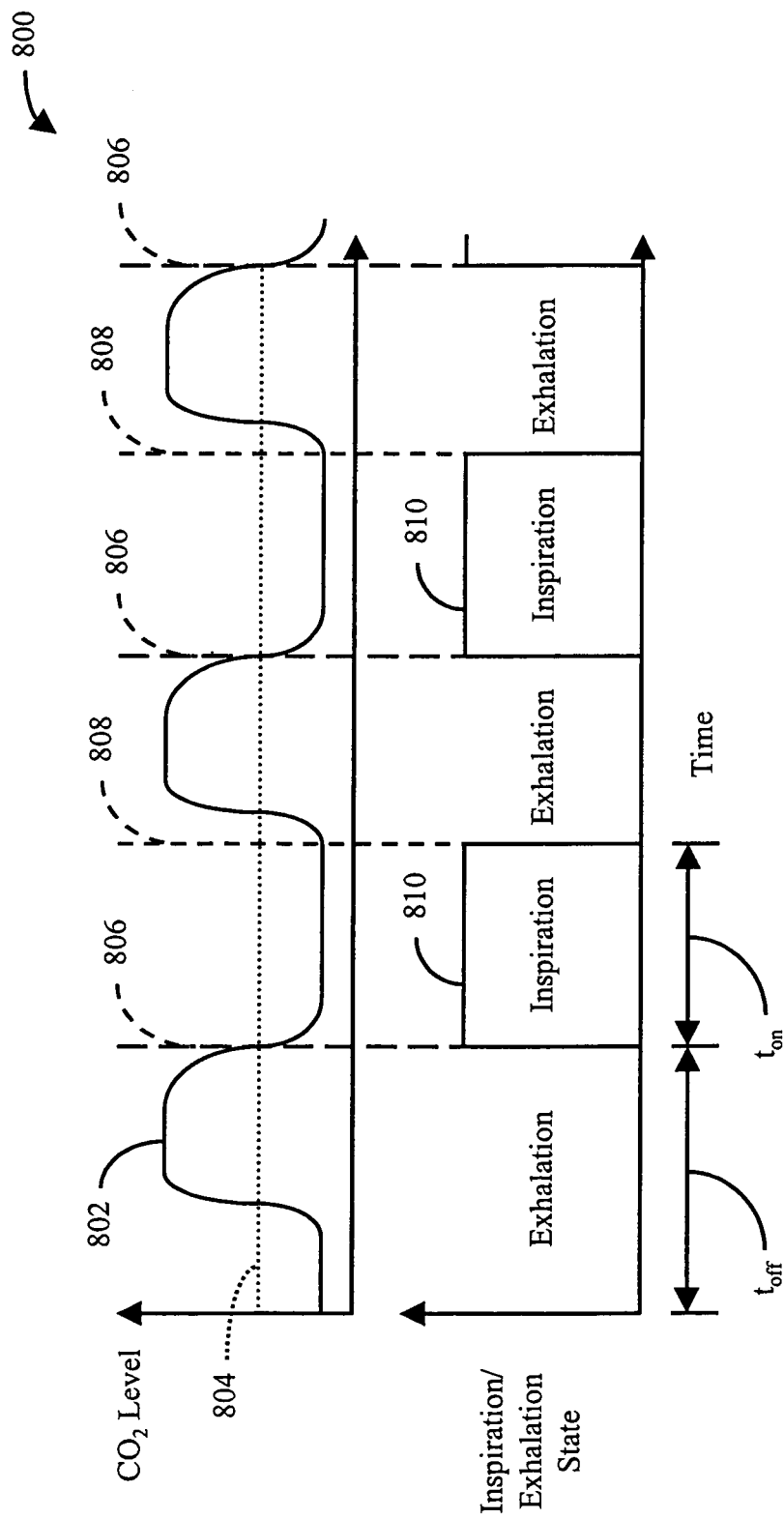
FIG. 8 illustrates a monostable timer control embodiment of the present invention.

Referring now to FIG. 8, a second embodiment of the present invention is illustrated that incorporates a monostable timer control to coordinate the IPAP and EPAP levels with the patient's breathing cycles. The monostable timer control can be implemented in any of the CPAP embodiments of FIGS. 1 through 4 wherein the monostable timer control is incorporated into bi-level CPAP logic 104.

In this regard, a monostable timer has one stable state and one quasi-stable state. For example, a timer having a variable off time and a fixed on time, or vice-versa, is generally known as a monostable timer. In the present embodiment, the variable off time of the monostable timer defines the exhalation state and the fixed on time defines the inhalation state. The opposite configuration can also be used. The monostable timer of the present invention also has a trigger in the form of a carbon-dioxide threshold level.

Referring now to FIG. 8 more particularly, the incorporation of a monostable timer control for governing the relationship between the level of carbon-dioxide associated with the patient breathing apparatus 114 and the inhalation and exhalation breathing states is generally illustrated at 800. In this regard, a representative carbon-dioxide level is shown over several patient breathing cycles is indicated by curve 802. As is commonly understood, more carbon-oxide is present in the patient breathing interface during exhalation than inhalation. Also illustrated is a threshold parameter 804 that serves to trigger the monostable timer of the present embodiment. Threshold parameter 804 is preferably defined as a carbon-dioxide level seen at the trailing or decreasing portion of the carbon-dioxide curve 802. The trigger points established by threshold parameter 804 are further illustrated by trigger lines 806. Hence, during patient exhalation, the level of carbon-dioxide increases over time to a certain level in the patient breathing interface or associated tubing. Venting by the patient breathing interface causes the carbon-dioxide level to begin decreasing. However, it is not until patient inhalation does the carbon-dioxide level decrease quickly over time so as to fall below threshold parameter 804 and trigger the monostable timer at 806.

In the present embodiment, during patient exhalation, the monostable timer is in its off state $t_{off}$ and micro-controller 102 directs blower 108 to provide an EPAP level to patient breathing interface 114. By providing an EPAP level, the patient can more comfortably exhale against a lower positive airway pressure. Once the carbon-dioxide level 802 rises and then falls below threshold parameter 804 to trigger the monostable timer at 806, the monostable timer changes to its on state $t_{on}$ for a fixed, predetermined time duration. This fixed, predetermined on time duration $t_{on}$ represents patient inhalation 810. The fixed, predetermined on time duration $t_{on}$ is based on the observation that during sleep most patient inhalation cycles have the same, or very nearly the same, duration. The monostable timer change of state from $t_{off}$ to $t_{on}$ causes micro-controller 102 to direct blower 108 to provide an IPAP level to the patient breathing interface 114 for the duration of time defined by $t_{on}$. By providing an IPAP level, a higher positive airway pressure is delivered to the patient during inhalation. Upon expiration of the time $t_{on}$, the monostable timer changes to its off state, as represented by lines 808. As described above, this causes micro-controller 102 to direct blower 108 to provide an EPAP level to the patient breathing interface 114 because the patient is about to exhale. The process is then repeated for the next patient breathing cycle.

Hence, the monostable timer control of the present invention provides a single trigger method for coordinating IPAP and EPAP levels with patient inhalation and exhalation. The trigger is defined by monitoring the carbon-dioxide level associated with the patient breathing interface for a falling level that crosses a predetermined threshold. The trigger defines a change in state of the monostable timer from an off state to an on state. The off state represents patient exhalation and causes the present invention to provide an EPAP level. The on state represents patient inhalation and causes the present invention to provide an IPAP level for a fixed, predetermined time duration. Upon expiration of the fixed, predetermined time duration, the present invention lowers the pressure back to EPAP level for patient exhalation. The process is repeated for each patient breathing cycle.

Figure 9:
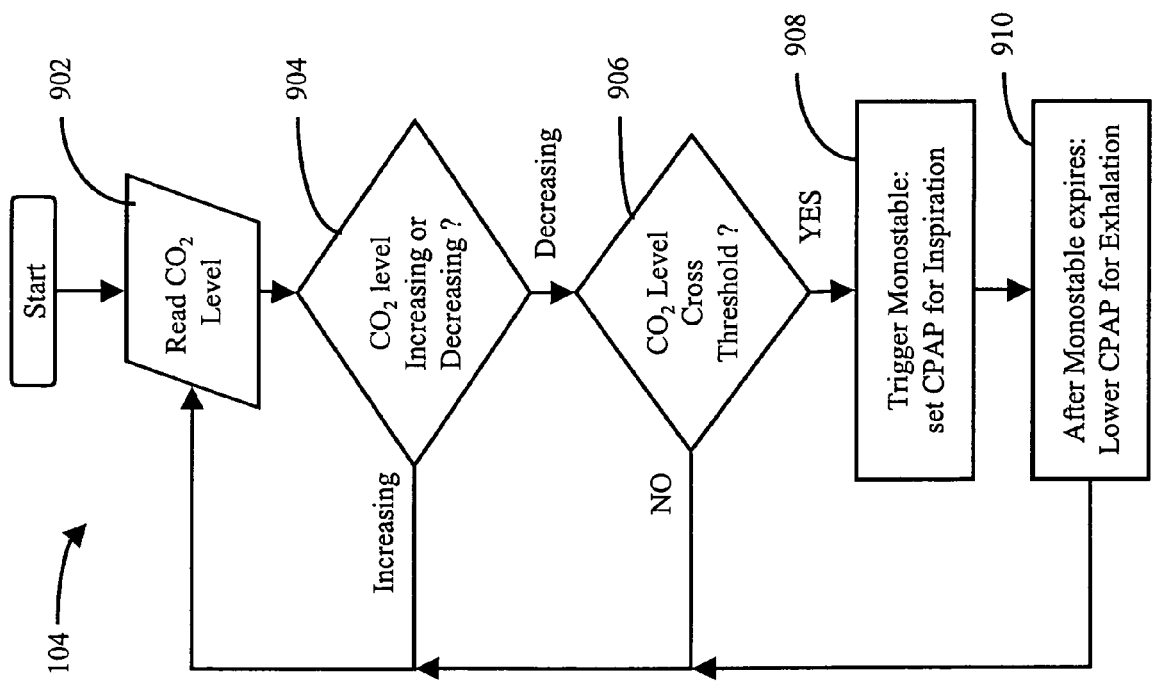
FIG. 9 is a flowchart of the monostable timer control logic of the present invention.

Referring now to FIG. 9, a flowchart illustrating the monostable timer control of bi-level CPAP logic 104 is shown. The logic commences in step 902 where the carbon-dioxide level associated with the patient breathing interface is sensed or monitored via carbon-dioxide sensor 116. Initially, the present invention provides an EPAP level until triggered. The logic then proceeds to step 904 where the sensed carbon-dioxide level is tested to determine whether it is increasing or decreasing. If the carbon-dioxide level is increasing, then the patient is exhaling and the EPAP level will continue to be provided. However, if the carbon-dioxide level is decreasing, the patient's breathing cycle is then starting a transition from exhalation to inhalation and the logic proceeds to step 906.

In step 906, the logic tests to determine whether the decreasing carbon-dioxide level has crossed a threshold parameter or value representing the state of patient inhalation. If the decreasing carbon-dioxide level has not crossed the threshold parameter, the logic loops back to step 902 to once again monitor the carbon-dioxide level. However, if the decreasing carbon-dioxide level has fallen to or below the threshold, then the logic advances to step 908 where the monostable timer is triggered to its on state. As described above, triggering the monostable timer causes an IPAP level to be delivered to the patient breathing interface for a fixed, predetermined time duration. Upon expiration of the fixed, predetermined time duration, the logic advances to step 910 where the monostable timer changes to its off state and an EPAP level is once again delivered to the patient breathing interface. After step 910, the logic loops back to step 902 and the process repeats. In this manner, a signal trigger is used to provide an IPAP level to a patient for a fixed, predetermined time duration for inhalation and an EPAP level to the patient for the duration of exhalation.

While the present invention has been illustrated by the description of embodiments thereof, and while the embodiments have been described in considerable detail, it is not the intention of application to restrict or in any way limit the scope of the appended claims to such detail. Additional advantages and modifications will readily appear to those skilled in the art. For example, the carbon-dioxide level can be quantitatively measured and used to raise or lower the IPAP or EPAP level in a step-wise fashion until obstructive sleep apnea no longer occurs. Still further, the carbon-dioxide sensor 116 of the present invention can be substituted with a temperature or humidity sensor. More specifically, exhalation and inhalation can be distinguished based on the temperature of the inhaled and exhaled gases. In this regard, exhaled gases have a higher temperature than inhaled gases and the temperature sensor would detect such a difference. Exhalation and inhalation can also be distinguished based on the water content or humidity level of the inhaled and exhaled gases. In this regard, exhaled gases have a higher humidity level than inhaled gases and the humidity sensor would detect such a difference. Still further, the present invention can be implemented with a microprocessor controlled system or discrete circuit element system. For example, a discrete circuit such as, for example, a Schmitt Trigger can be used to sense the carbon-dioxide level. Therefore, the invention, in its broader aspects, is not limited to the specific details, the representative apparatus, and illustrative examples shown and described. Accordingly, departures may be made from such details without departing from the spirit or scope of the applicant's general inventive concept.

What is claimed is:

1. A system for administering a breathing gas comprising:
    a patient breathing interface;
    a blower for providing positive pressure breathing gas to the patient breathing interface;
    a controller in circuit communication with the blower; and
    an infrared light emitter and detector in circuit communication with the controller for detecting the level of carbon-dioxide associated with the patient breathing interface,
    wherein the controller comprises logic to control the blower to increase the pressure of the positive pressure breathing gas in response to the patient inhaling as indicated by the level of carbon-dioxide detected and decrease the pressure of the positive pressure breathing gas in response to the patient exhaling as indicated by the level of carbon-dioxide detected to maintain open the airway of a patient.

2. The system of claim 1 wherein the controller further comprises logic for comparing the level of carbon-dioxide associated with the patient breathing interface to a threshold parameter.

3. The system of claim 1 further comprising a timer having a variable off time period and predetermined on time period.

4. The system of claim 1 further comprising optical fibers coupled to the infrared emitter and detector.

5. The system of claim 1 wherein the infrared emitter and detector are located within a housing accommodating the controller.

6. The system of claim 1 wherein the patient breathing interface comprises a vent, and wherein the infrared emitter and detector are located proximate to the vent.

7. A system for administering a breathing gas to a patient comprising:
    a patient breathing interface;
    a subsystem capable of providing variable positive pressure breathing gas to the patient breathing interface;
    a controller in circuit communication with the subsystem; and
    a carbon dioxide detector in communication with the patient breathing interface for detecting whether the patient is inhaling or exhaling,
    wherein the controller comprises logic to control the subsystem responsive to the carbon dioxide detector to cause the subsystem to provide a first pressure of the positive pressure breathing gas in response to the patient inhaling as indicated by the level of carbon-dioxide detected and to provide a second pressure of the positive pressure breathing gas in response to the patient exhaling as indicated by the level of carbon-dioxide detected.

8. The system of claim 7, wherein the subsystem comprises a blower.

9. The system of claim 8, wherein the subsystem comprises a driver capable of driving the blower through a range of variable speeds.

10. The system of claim 7, wherein the detector comprises an infrared light emitter and detector.

11. The system of claim 7, wherein the controller further comprises logic for comparing a level of carbon dioxide detected in the patient breathing interface by the detector to a threshold parameter.

12. The system of claim 11, further comprising at least one input device in communication with the controller to enable input of a desired value for the threshold parameter.

13. The system of claim 7, further comprising an input device in communication with the controller to enable input of a desired value for at least one of the first pressure and the second pressure.

14. The system of claim 7, further comprising a device in communication with the controller and capable of causing the subsystem to provide the first pressure of the positive pressure breathing gas for a fixed time period.

15. The system of claim 14, wherein the device comprises a timer.

16. A system for administering breathing gas comprising:
   a patient breathing interface;
   a variable speed blower providing variable positive pressure breathing gas to the patient breathing interface;
   a controller in circuit communication with the blower;
   (a) an infrared light emitter and detector in communication with the patient breathing interface for detecting the level of carbon-dioxide associated with the patient breathing interface to determine whether a patient is inhaling or exhaling;
   wherein the controller comprises logic to control the variable speed blower responsive to the infrared light detector to cause the variable speed blower to provide a first pressure of the positive pressure breathing gas in response to the patient inhaling as indicated by the level of carbon-dioxide detected and to provide a second pressure of the positive pressure breathing gas in response to the patient exhaling as indicated by the level of carbon-dioxide detected; and
   (b) at least one input device in communication with the controller to enable input of a desired value for a threshold parameter and at least one of the first pressure and the second pressure;
   wherein the controller further comprises logic for comparing a level of carbon dioxide detected in the patient breathing interface by the detector to the threshold parameter.

17. A system for administering a breathing gas to a patient comprising:
   a patient breathing interface;
   means for providing variable positive pressure breathing gas to the patient breathing interface;
   means for determining whether the patient is inhaling or exhaling based on detection of carbon dioxide in the patient breathing interface; and
   means for maintaining open the airway of the patient by causing a first pressure of the positive pressure breathing gas to be provided to the patient breathing interface in response to the patient inhaling as indicated by the level of carbon-dioxide detected and for causing a second pressure of the positive pressure breathing gas to be provided to the patient breathing interface in response to the patient exhaling as indicated by the level of carbon-dioxide detected.

18. The system of claim 17, further comprising means for detecting carbon dioxide.

\* \* \* \* \*